United States Patent [19]

Tornier

[11] Patent Number: 4,488,543
[45] Date of Patent: Dec. 18, 1984

[54] DEVICE FOR OSTEOSYNTHESIS OF FRACTURES OF THE EXTREMITIES OF THE FEMUR

[75] Inventor: Alain Tornier, Iséres, France

[73] Assignees: Tornier S.A. France, St. Ismier; Jean Butel, Meylan, both of France

[21] Appl. No.: 459,250

[22] Filed: Jan. 19, 1983

[30] Foreign Application Priority Data

Jan. 19, 1982 [FR] France .................. 82 01126

[51] Int. Cl.³ .................. A61F 1/04; A61B 17/18
[52] U.S. Cl. .................. 128/92 BB; 128/92 D; 128/92 G
[58] Field of Search .......... 128/92 BB, 92 BA, 92 R, 128/92 D, 92 G

[56] References Cited

U.S. PATENT DOCUMENTS 3,842,825 10/1974 Wagner .................. 128/92 BB

FOREIGN PATENT DOCUMENTS 2289154 5/1976 France .................. 128/92 BA
2405062 6/1979 France .................. 128/92 D

*Primary Examiner*—Ronald L. Frinks
*Attorney, Agent, or Firm*—Browdy & Neimark

[57] ABSTRACT

A device for osteosynthesis of the fractures of the extremities of the femur comprises a plate in which holes are provided for the passage of screws intended to be inserted into the bone to make the fractured bone and the plate solid.

One end of the plate to be applied against one of extremities of the femur is wider than the other end and includes three holes arranged in an isosceles triangle. The median plane of the one end defines a plane which forms, with the plane of the rest of the plate, an obtuse angle of between 160° and 175°.

4 Claims, 3 Drawing Figures

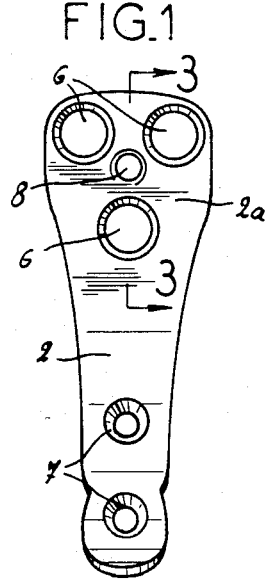
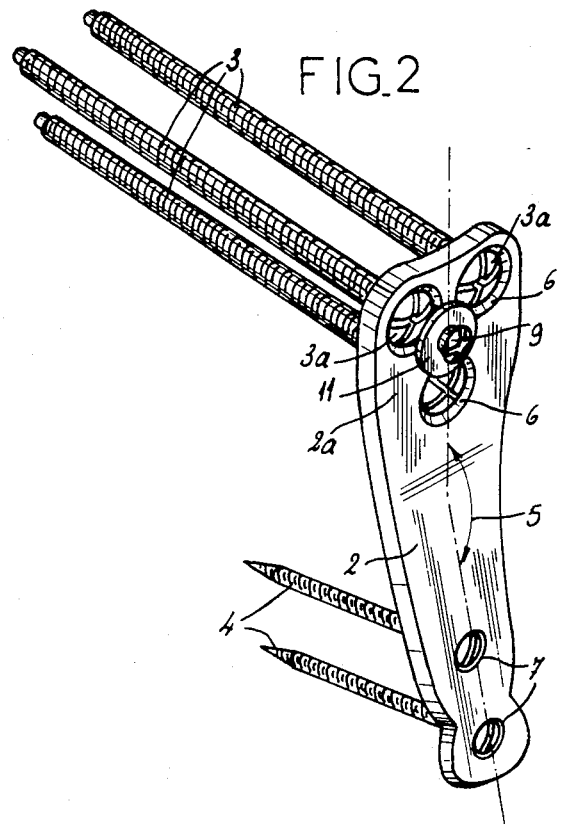
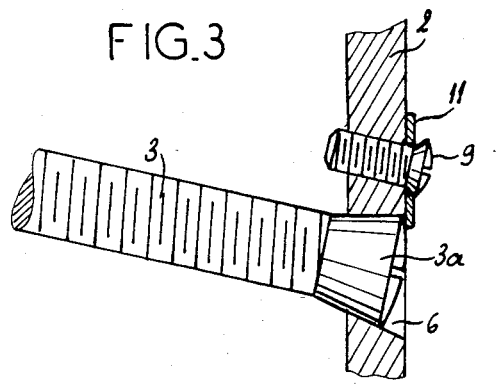

DEVICE FOR OSTEOSYNTHESIS OF FRACTURES OF THE EXTREMITIES OF THE FEMUR

BACKGROUND OF THE INVENTION

This invention relates to a device for osteosynthesis of fractures of the extremities of the femur. This device is of the type comprising a plate in which holes are provided for the passage of screws intended to be inserted into the bone to make the parts of fractured bone and the plate solid.

In the device according to the invention, the end of the plate to be applied against one of the extremities of the femur exhibits a widening to provide for three holes which form an isosceles triangle while the rest of the plate forms, with the median plane of the extremity, an obtuse angle between 160° and 175°.

This arrangement, therefore, makes possible a very good application of the plate against the diaphysis and the corresponding extremity of the bone that it fits perfectly.

Further, the triangle arrangement of the holes in the end of the plate applied against one of the ends of the bone makes possible a peripheral attachment in triangulation in the femoral neck or head for the upper extremity of the femur and in the femoral condyles for its lower extremity.

Another advantage of the invention is that the heads of the screws to be inserted in the holes are shaped as truncated cones and the holes are complementarily configured. This arrangement makes possible a solid and proper attachment of the femoral head in the cervical fractures, a solid hold with a possibility of correcting the varus in per-, inter- or sub-trochanteric, or even trochanterodiaphyseal fractures for the extremity of the femur.

According to yet another characteristic of the invention, in the center of the triangle formed by the three conical holes in the enlarged end of the plate is a threaded hole for insertion of an auxiliary screw that is used for attaching a disk whose outer diameter makes it possible to partially cover the conical heads of the screws inserted in said three conical holes.

This disk assures the holding of the three screws under consideration and prevents their backward movement during the compression under load of the fracture.

Preferably this disk is elastic to make possible the passage of the screw heads and the backward movement of the screw heads if they were to come in contact with the cortical of the femoral head.

This arrangment, therefore, has the advantage of increasing the mechanical behavior of this device by taking all the advantages of one-piece mountings, while avoiding the risks of deterioration by perforation of the corticals of the femoral head and keeping the simplicity of a screwed-on mounting.

BRIEF DESCRIPTION OF THE DRAWINGS

The invention will be better understood from the description which follows, with reference to the accompanying diagrammatic drawing that represents, by way of non-limiting example, an embodiment of this device:

FIG. 1 is a top plan view of the plate alone;

FIG. 2 is a view in perspective showing the plate and the screws; and

FIG. 3 is, on a larger scale, a partial view in section along section line 3—3 of FIG. 1, after a screw has been put in place.

DETAILED DESCRIPTION OF THE INVENTION

As the drawing shows, this device is of the type having a plate 2 and screws 3 and 4. As particularly shown in FIG. 1, one end 2a of plate 2, i.e., more precisely the one which is intended to be applied against one of the extremities of the femur, is widened, and defines or lies in a plane which forms, with the plane of the rest of the plate, an angle 5 between 160° and 175°. This angling has as its object to make possible a good application of this end of the plate against the extremity of the femur concerned.

The wide extremity 2a of this plate 2 includes three holes 6 each having the shape of a truncated cone arranged in an isosceles triangle for the passage of screws 3 which are the thickest used in combination with this plate since they are to be implanted in the femoral head or in the femoral condyles. The triangular arrangement of holes 6 facilitates an attachment in triangulation of the extremity of the femur under consideration, thereby providing a better balance of the attachment forces during osteosynthesis.

The other, more narrow part of plate 2, intended to be applied against the diaphysis of the femur, includes holes 7 of a standard type for the passage of screws 4 of smaller dimensions than screws 3.

As shown in FIG. 3, head 3a of each screw 3 is a truncated conical shape and its dimensions are such that it is complimentary with a hole 6 in a shape of a truncated cone which is able to be used as housing for it.

As shown in FIG. 1, a threaded hole 8 is advantageously provided for receipt of a screw 9 which facilitates attachment of a disk 11. The disk has centrally between the three holes a diameter which partially covers each of heads 3a of screws 3 to assure their being held in corresponding holes 6.

This arrangement prevents, therefore, the backward movement of screws 3 out of holes 6 during the compression under load of the fracture.

Advantageously, disk 11 is elastic thereby making possible the passage of heads 3a of screws 3 and the backward movements of the screws 3, in the event that they come in contact with the cortical of the femoral head.

This arrangement eliminates the risk of deterioration by perforation of the corticals of the femoral head.

Preferably, the threading of screw 9 and the threading of hole 8 which correspond, are at least partially conical so as to assure a very good attachment of screw 9 in this hole 8.

It is apparent from the foregoing that once the broad aspects of the invention are disclosed, many embodiments thereof will be readily occur to those skilled in the art, as well as many modifications of the embodiments here disclosed. Accordingly, it is intended that the foregoing disclosure be considered purely illustrative, and not limiting in any sense.

What is claimed is:

1. In a device for osteosynthesis of the fractures of the extremities of the femur of the type having a plate including a plurality of holes and a screw for insertion in each hole to insure rigid attachement between the parts of the fractured bone and the plate, the improvement comprising:

one end of said plate being attachable to one of the extremities of the femur being wider than the other end, said wider end including three holes arranged in an isosceles triangle, the heads of said screws having the shape of a truncated cone, and said holes exhibiting a complementarily shaped recess so that each recess can house the head of a said screw, said wider end defining a plane which forms, with the plane of the rest of said plate, an angle between 160° and 175°, and a threaded opening at the center of the triangle formed by said three conical holes, and an auxiliary screw for insertion through said opening, and a disk, the outer diameter of said disk partially covering the conical heads of said three screws when carried in said three conical holes.

2. The improvement according to claim 1, wherein said disk is elastic to make possible, by its elastic deformation, the possible passage of one or more of the heads of said screws.

3. The improvement according to claim 2, wherein the threads of said opening and said auxiliary screw are at least partially conical.

4. The improvement according to claim 1, wherein the threads of said opening and said auxiliary screw are at least partially conical.